(12) United States Patent
Hergenrother et al.

(10) Patent No.: US 9,399,035 B2
(45) Date of Patent: Jul. 26, 2016

(54) PROCASPASE 3 ACTIVATION BY COMBINATION THERAPY

(71) Applicants: Paul J. Hergenrother, Champaign, IL (US); Rachel C. Botham, Champaign, IL (US); Timothy M. Fan, Mahomet, IL (US); Mark J. Gilbert, Seattle, WA (US); Michael K. Handley, Windsor, CO (US); Howard S. Roth, Champaign, IL (US); Theodore M. Tarasow, San Ramon, CA (US)

(72) Inventors: Paul J. Hergenrother, Champaign, IL (US); Rachel C. Botham, Champaign, IL (US); Timothy M. Fan, Mahomet, IL (US); Mark J. Gilbert, Seattle, WA (US); Michael K. Handley, Windsor, CO (US); Howard S. Roth, Champaign, IL (US); Theodore M. Tarasow, San Ramon, CA (US)

(73) Assignees: The Board of Trustees of the University of Illinois, Urbana, IL (US); Vanquish Oncology, Inc., Champaign, IL (US)

( * ) Notice: Subject to any disclaimer, the term of this patent is extended or adjusted under 35 U.S.C. 154(b) by 0 days.

(21) Appl. No.: 14/383,441

(22) PCT Filed: Mar. 6, 2013

(86) PCT No.: PCT/US2013/029405
§ 371 (c)(1),
(2) Date: Sep. 5, 2014

(87) PCT Pub. No.: WO2013/134407
PCT Pub. Date: Sep. 12, 2013

(65) Prior Publication Data
US 2015/0017264 A1    Jan. 15, 2015

Related U.S. Application Data

(60) Provisional application No. 61/607,098, filed on Mar. 6, 2012.

(51) Int. Cl.
| | | |
|---|---|---|
| A61K 33/24 | (2006.01) | |
| A61K 31/495 | (2006.01) | |
| A61K 31/496 | (2006.01) | |
| A61K 45/06 | (2006.01) | |
| A61K 9/00 | (2006.01) | |
| A61K 47/10 | (2006.01) | |
| A61K 9/08 | (2006.01) | |
| A61K 9/20 | (2006.01) | |
| A61K 9/48 | (2006.01) | |
| A61K 31/138 | (2006.01) | |
| A61K 31/282 | (2006.01) | |
| A61K 31/337 | (2006.01) | |
| A61K 31/553 | (2006.01) | |
| A61K 31/704 | (2006.01) | |
| A61K 31/7048 | (2006.01) | |
| A61K 38/05 | (2006.01) | |

(52) U.S. Cl.
CPC ............... *A61K 31/495* (2013.01); *A61K 9/008* (2013.01); *A61K 9/0019* (2013.01); *A61K 9/08* (2013.01); *A61K 9/2027* (2013.01); *A61K 9/2054* (2013.01); *A61K 9/2059* (2013.01); *A61K 9/4858* (2013.01); *A61K 31/138* (2013.01); *A61K 31/282* (2013.01); *A61K 31/337* (2013.01); *A61K 31/496* (2013.01); *A61K 31/553* (2013.01); *A61K 31/704* (2013.01); *A61K 31/7048* (2013.01); *A61K 33/24* (2013.01); *A61K 38/05* (2013.01); *A61K 45/06* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 6,303,329 B1 | 10/2001 | Heinrikson et al. | |
| 6,403,765 B1 | 6/2002 | Alnemri | |
| 6,534,267 B1 | 3/2003 | Wang et al. | |
| 6,762,045 B2 | 7/2004 | Krebs et al. | |
| 6,878,743 B2 | 4/2005 | Choong et al. | |
| 7,041,784 B2 | 5/2006 | Wang et al. | |
| 7,632,972 B2 | 12/2009 | Hergenrother et al. | |
| 8,592,584 B2 * | 11/2013 | Hergenrother et al. | ........ 544/357 |
| 8,778,945 B2 * | 7/2014 | Hergenrother et al. | .. 514/252.12 |
| 2004/0077542 A1 * | 4/2004 | Wang et al. | ..................... 514/12 |
| 2004/0180828 A1 | 9/2004 | Shi | |
| 2007/0049602 A1 * | 3/2007 | Hergenrother et al. | .. 514/252.12 |
| 2010/0291214 A1 | 11/2010 | Gabriele et al. | |
| 2011/0257398 A1 | 10/2011 | Hergenrother et al. | |
| 2012/0040995 A1 | 2/2012 | Hergenrother et al. | |

FOREIGN PATENT DOCUMENTS

| | | |
|---|---|---|
| RU | 2410389 C2 | 9/2006 |
| RU | 2439695 C2 | 11/2006 |
| RU | 2360692 C1 | 12/2007 |
| RU | 2408584 C2 | 1/2011 |
| WO | 2007137200 A2 | 11/2007 |

(Continued)

OTHER PUBLICATIONS

STN CAS RN 1103440 60 3 entered Feb. 9, 2009.*

(Continued)

*Primary Examiner* — Jared D Barsky
(74) *Attorney, Agent, or Firm* — Haukaas Fortius PLLC; Michael Haukaas

(57) ABSTRACT

The invention provides compositions and methods for the induction of cell death, for example, cancer cell death. Combinations of compounds and related methods of use are disclosed, including the use of compounds in therapy for the treatment of cancer and selective induction of apoptosis in cells. The disclosed drug combinations can have lower neurotoxicity effects than other compounds and combinations of compounds.

5 Claims, 10 Drawing Sheets

(56) References Cited

FOREIGN PATENT DOCUMENTS

| WO | 2008134474 A2 | 11/2008 |
|---|---|---|
| WO | 2009089508 A1 | 7/2009 |

OTHER PUBLICATIONS

Yang et al., "The p53-dependent apoptotic pathway of breast cancer cells (BC-M1) induced by the bis-type bioreductive compound aziridinylnaphthoquinone," Breast Cancer Res. 2005;7(1):R19-27 Epub Nov. 4, 2004.*

Peterson et al., "Discovery and Canine Preclinical Assessment of a Nontoxic Procaspase-3-Activating Compound," Cancer Research, Sep. 15, 2010. 70: pp. 7232-7241.

Peterson et al., "PAC-1 Activates Procaspase-3 in Vitro through Relief of Zinc-Mediated Inhibition," J. Mol. Biol., Mar. 10, 2009. 388: pp. 144-158.

Peterson et al., "Procaspase-3 Activation as an Anti-Cancer Strategy: Structure-Activity Relationship of Procaspase-Activating Compound 1 (PAC-1) and Its Cellular Co-Localization with Caspase-3," J. Med. Chem., Aug. 8, 2009. 59: pp. 5721-5731.

Putt et al., "Small-molecule activation of procaspase-3 to caspase-3 as a personalized anticancer strategy," Nat. Chem. Biol., Oct. 2006. 2: pp. 543-550.

Wolan et al., "Small-Molecule Activators of a Proenzyme," Science Mag, 2009. 326: pp. 852-858.

Zorn et al., "Self-Assembling Small Molecules Form Nanofibrils That Bind Procaspase-3 to Promote Activatoin," J. of the American Chem. Soc., Nov. 8, 2011., 133: pp. 19630-19633.

International Search Report and Written Opinion for PCT/US2013/029405, dated Mar. 6, 2013, 3 pp.

International Preliminary Report on Patentability for PCT/US2013/029405 dated Mar. 6, 2013, 7 pp.

\* cited by examiner

PROCASPASE 3 ACTIVATION BY COMBINATION THERAPY

RELATED APPLICATIONS

This application claims priority under 35 U.S.C. §119(e) to U.S. Provisional Patent Application No. 61/607,098, filed Mar. 6, 2012, which is incorporated herein by reference.

BACKGROUND OF THE INVENTION

Apoptosis, or programmed cell death, plays a central role in the development and homeostasis of all multicellular organisms. A frequent hallmark of cancer is resistance to natural apoptotic signals. Depending on the cancer type, this resistance is typically due to up- or down-regulation of key proteins in the apoptotic cascade or to mutations in genes encoding these proteins. Such changes occur in both the intrinsic apoptotic pathway, which funnels through the mitochondria and caspase-9, and the extrinsic apoptotic pathway, which involves the action of death receptors and caspase-8. For example, alterations in proper levels of proteins such as p53, Bim, Bax, Apaf-1, FLIP and many others have been observed in cancers. The alterations can lead to a defective apoptotic cascade, one in which the upstream pro-apoptotic signal is not adequately transmitted to activate the executioner caspases, caspase-3 and caspase-7.

As most apoptotic pathways ultimately involve the activation of procaspase-3, upstream genetic abnormalities are effectively "breaks" in the apoptotic circuitry, and as a result such cells proliferate atypically. Given the central role of apoptosis in cancer, efforts have been made to develop therapeutics that target specific proteins in the apoptotic cascade. For instance, peptidic or small molecule binders to cascade members such as p53 and proteins in the Bcl family or to the inhibitor of apoptosis (IAP) family of proteins have pro-apoptotic activity, as do compounds that promote the oligomerization of Apaf-1. However, because such compounds target early (or intermediate to high) positions on the apoptotic cascade, cancers with mutations affecting proteins downstream of those members can still be resistant to the possible beneficial effects of those compounds.

It would be advantageous for therapeutic purposes to identify small molecules that directly activate a proapoptotic protein far downstream in the apoptotic cascade. This approach could involve a relatively low position in the cascade, thus enabling the killing of even those cells that have mutations that affect upstream apoptotic machinery. Moreover, such therapeutic strategies would have a higher likelihood of success if that proapoptotic protein were upregulated or present at increased levels in cancer cells. Thus, the identity of small molecules that target the downstream effector protein of apoptosis, procaspase-3, would significantly aid current cancer therapy.

The conversion or activation of procaspase-3 to caspase-3 results in the generation of the active "executioner" caspase form that subsequently catalyzes the hydrolysis of a multitude of protein substrates. Active caspase-3 is a homodimer of heterodimers and is produced by proteolysis of procaspase-3. In vivo, this proteolytic activation typically occurs through the action of caspase-8 or caspase-9. To ensure that the zymogen (proenzyme) is not prematurely activated, procaspase-3 has a 12 amino acid "safety catch" that blocks access to the ETD site (amino acid sequence, ile-glu-thr-asp) of proteolysis. This safety catch enables procaspase-3 to resist autocatalytic activation and proteolysis by caspase-9. Mutagenic studies indicate that three consecutive aspartic acid residues appear to be the critical components of the safety catch. The position of the safety catch is sensitive to pH, thus upon cellular acidification (as occurs during apoptosis) the safety catch is thought to allow access to the site of proteolysis, and active caspase-3 can be produced either by the action of caspase-9 or through an autoactivation mechanism.

In certain cancers, the levels of procaspase-3 are elevated relative to normal tissue. A study of primary isolates from 20 colon cancer patients revealed that on average, procaspase-3 was upregulated six-fold in such isolates relative to adjacent non-cancerous tissue. In addition, procaspase-3 is upregulated in certain neuroblastomas, lymphomas, and liver cancers. Furthermore, a systematic evaluation was performed of procaspase-3 levels in the 60 cell-line panel used for cancer screening by the National Cancer Institute (NCI) Developmental Therapeutics Program, which revealed that certain lung, melanoma, renal, and breast cancers show greatly enhanced levels of procaspase-3 expression.

Due to the role of active caspase-3 in achieving apoptosis, the relatively high levels of procaspase-3 in certain cancerous cell types, and the intriguing safety catch-mediated suppression of its autoactivation, small molecules that directly modify procaspase-3 could have great applicability in targeted cancer therapy.

Combination therapy has become standard for treatment of cancer patients. The goal of combination therapy drug cocktail regimes is to achieve a synergistic or additive effect between chemotherapeutics, thereby facilitating shortened treatment times, decreased toxicity, and increased patient survival. Drugs that act on a single biochemical pathway are particularly strong candidates for synergy or potentiation as they may mimic "synthetic lethal" genetic combinations. For example, inhibitors of poly(ADP-ribose)polymerase-1 (PARP-1), an enzyme that facilitates DNA damage repair, potently synergize with DNA damaging agents as demonstrated in cell culture, animal models, and human clinical trials. However, there is still a need for more effective therapies for the treatment of many forms of cancer, and new synergistic combinations of anticancer drugs would aid this pursuit. Accordingly, there exists a need to identify new cytotoxic agents that are effective in killing cancer cells yet protect normal host tissues from the undesired toxicity of the cytotoxic agent.

SUMMARY

The invention broadly provides compounds, compositions, and methods of therapeutic treatment. In various embodiments, the inventions are applicable to a variety of cancer diseases and cancer cell types such as breast, lymphoma, adrenal, renal, melanoma, leukemia, neuroblastoma, lung, brain, and others known in the art. Herein is disclosed, inter alia, compositions and methods including small molecules capable of inducing cell death. In some embodiments, the compositions and methods involve compounds that can interact directly or indirectly with programmed cell death pathway members such as procaspase-3. In certain embodiments, the compositions and methods have reduced neurotoxicity compared to other compounds that interact directly or indirectly with programmed cell death pathway members such as procaspase-3.

Combination anticancer therapy can consist of drugs that target different biochemical pathways, or those that hit different targets in the same pathway, mimicking "synthetic lethal" genetic combinations. The combination of the procaspase-3 activator PAC-1 and a second active agent has shown considerable synergy toward inducing apoptotic death of cancer cells, often to a degree well exceeding the additive effect. The combination of PAC-1 and a second active agent can be used to effectively reduce tumor burden in tumor models in which the compounds alone have minimal or no effect. The data described herein indicate the efficacy of a PAC-1/second agent combination for the treatment of cancer and, more broadly, show that the combinations can be synergistic and provide significantly heightened therapeutic benefits.

Accordingly, the invention provides a composition comprising:
(a) the compound PAC-1:

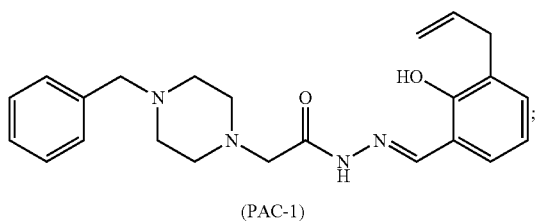 [SMILES: C=CCc1cccc(/C=N/NC(=O)CN2CCN(Cc3ccccc3)CC2)c1O]

(PAC-1)

(b) a second active agent; and (c) a pharmaceutically acceptable diluent, excipient, or carrier. The second active agent can be, for example, etoposide, bortezomib, staurosporine, doxorubicin, tamoxifen, cisplatin, carboplatin, paclitaxel, or another chemotherapeutic or otherwise active agent recited herein. The carrier can include water and optional components for advantageously delivering the actives such as a buffer, a sugar, solubilization agents such as a cyclodextrin, or various combinations thereof. In one embodiment, the cyclodextrin is 2-hydroxypropyl-β-cyclodextrin.

The concentration of PAC-1 can be about 0.2 μM to about 5 mM, or about 2 μM to about 50 μM, typically about 2.5 μM, about 5 μM, about 7.5 μM, about 10 μM, about 12.5 μM, about 15 μM, about 20 μM, about 25 μM, about 30 μM, about 40 μM, or about 50 μM, or a range between any of the aforementioned values. The concentration of the second active agent can be about 1 nM to about 1 mM, or about 25 nM to about 1 mM, typically about 1 nM, about 2 nM, about 3 nM, about 5 nM, about 10 nM, about 25 nM, about 50 nM, about 100 nM, about 250 nM, about 500 nM, about 750 nM, about 900 nM, about 1 μM, about 2.5 μM, about 5 μM, about 7.5 μM, about 10 μM, about 12.5 μM, about 15 μM, about 20 μM, about 25 μM, about 30 μM, about 40 μM, about 50 μM, about 75 μM, about 100 μM, about 125 μM, about 150 μM, about 200 μM, about 250 μM, about 300 μM, about 500 μM, about 750 μM, or about 1 mM, or a range between any of the aforementioned values.

In one embodiment, the second active agent can be etoposide and the concentration of etoposide can be about 0.2 μM to about 50 μM.

In another embodiment, the second active agent can be bortezomib and the concentration of bortezomib can be about 50 nM to about 20 μM.

In another embodiment, the second active agent can be staurosporine and the concentration of staurosporine can be about 25 nM to about 200 nM.

In another embodiment, the second active agent can be doxorubicin and the concentration of doxorubicin can be about 50 nM to about 5 μM.

In another embodiment, the second active agent can be tamoxifen and the concentration of tamoxifen can be about 5 μM to about 50 μM.

In another embodiment, the second active agent can be cisplatin and the concentration of cisplatin can be about 5 μM to about 150 μM.

In another embodiment, the second active agent can be carboplatin and the concentration of carboplatin can be about 5 μM to about 150 μM.

In another embodiment, the second active agent can be paclitaxel and the concentration of paclitaxel can be about 0.5 nM to about 15 nM.

The invention also provides a method of inhibiting the growth or proliferation of cancer cells comprising contacting cancer cells with an effective amount of a composition of described herein, thereby inhibiting the growth or proliferation of the cancer cells. In some embodiments, the cancer cells can be lymphoma cells, osteosarcoma cells, breast cancer cells, or ovarian cancer cells. In another embodiment, the cancer cells are another cell type described herein below.

The invention further provides a method of inducing apoptosis in a cancer cell comprising contacting the cancer cell with an effective amount of the compound PAC-1:

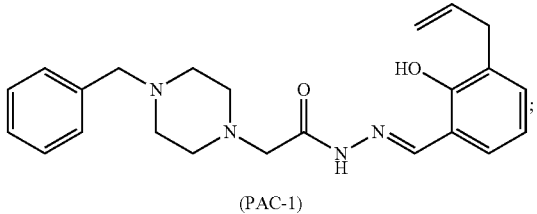 [SMILES: C=CCc1cccc(/C=N/NC(=O)CN2CCN(Cc3ccccc3)CC2)c1O]

(PAC-1)

and an effective amount of a second active agent; wherein apoptosis is thereby induced in the cancer cell. In some embodiments, the second active agent is etoposide, bortezomib, staurosporine, doxorubicin, tamoxifen, cisplatin, carboplatin, or paclitaxel. In other embodiments, the second active agent is an active agent recited herein below. The contacting can be in vitro, or the contacting can be in vivo. The cancer cell can be contacted with PAC-1 and the second active agent concurrently. Alternatively, the cancer cell can be contacted with PAC-1 prior to contacting the cancer cell with the second active agent, or the cancer cell can be contacted with PAC-1 after contacting the cancer cell with the second active agent.

The invention yet further provides a method of treating a cancer in a patient in need thereof comprising administering to a patient, concurrently or sequentially, a therapeutically effective amount of the compound PAC-1:

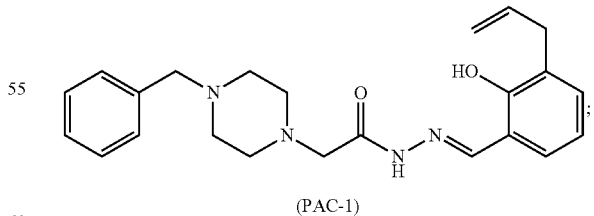

(PAC-1)

and an effective amount of a second active agent; wherein the cancer is thereby treated. In some embodiments, the second active agent is etoposide, bortezomib, staurosporine, doxorubicin, tamoxifen, cisplatin, carboplatin, or paclitaxel. In other embodiments, the second active agent is an active agent recited herein below. The compound PAC-1 and the second active agent can be administered concurrently. Alternatively, the compound PAC-1 and the second active agent can be administered sequentially. In one embodiment, the compound PAC-1 is administered before the second active agent. In another embodiment, the compound PAC-1 can be administered after the second active agent. The cancer can be, for example, lymphoma, osteosarcoma, breast cancer, ovarian cancer, or another cancer type recited herein.

The invention thus provides for the use of the compositions described herein for use in medical therapy. The medical therapy can be treating cancer, for example, lymphoma, breast cancer, lung cancer, ovarian cancer, pancreatic cancer, prostate cancer, colon cancer, and other cancers recited herein. The invention also provides for the use of a composition as described herein for the manufacture of a medicament to treat a disease in a mammal, for example, cancer in a human. The invention thus provides for the use of the compounds described herein for the manufacture of medicaments useful for the treatment of cancer in a mammal, such as a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
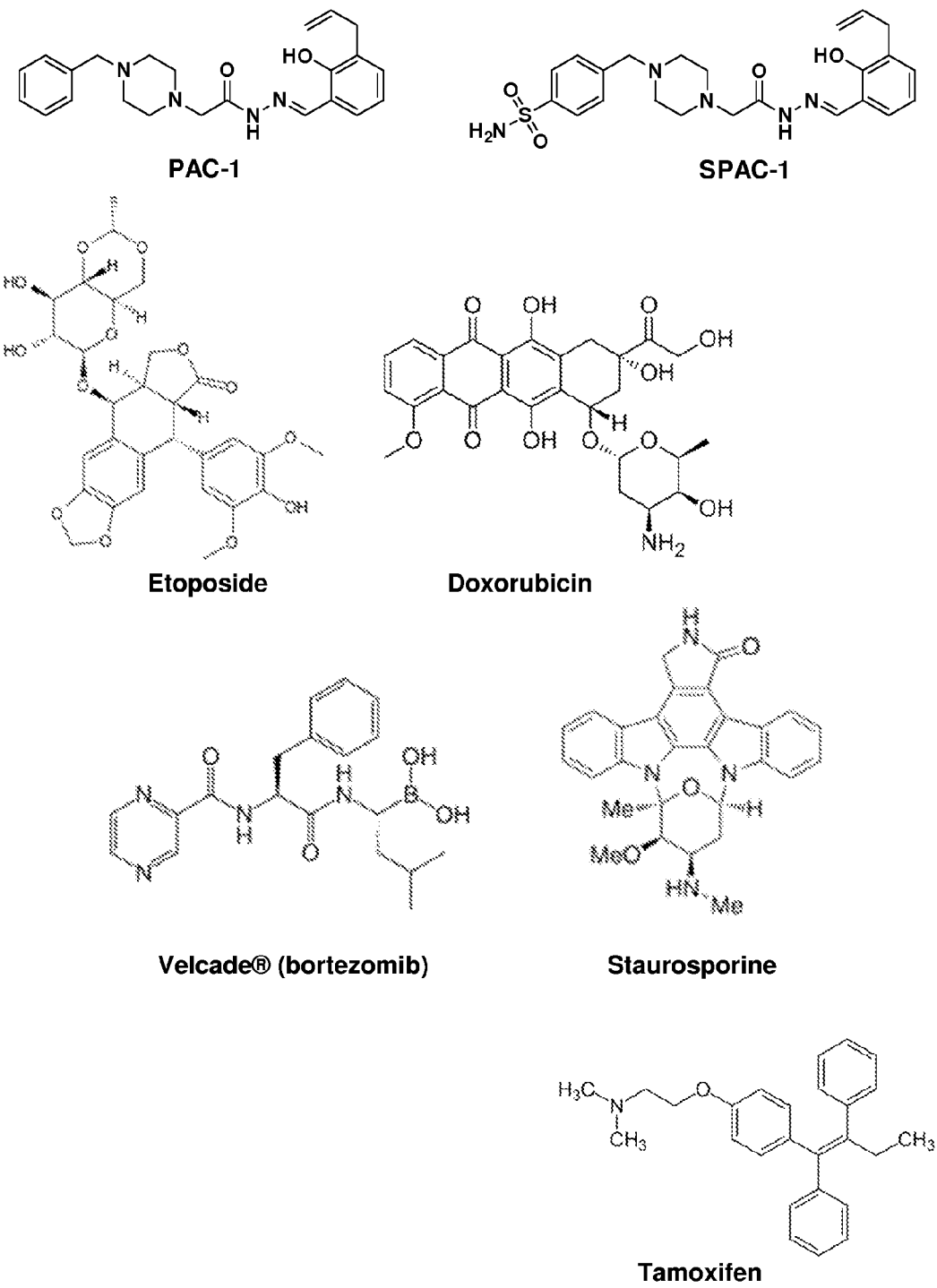
FIG. 1. Chemical structures of structurally diverse chemotherapeutic agents: PAC-1, SPAC-1, etoposide, doxorubicin, bortezomib, staurosporine, and tamoxifen.

As a further introduction, compounds capable of activating an enzyme that is often overexpressed or otherwise present at increased levels in its inactive form in cancer cells have been discovered. The compounds can induce programmed cell death (apoptosis) in cancer cells, including those that have upregulated or increase levels of procaspase-3. Many cancers resist standard chemotherapy. The combination therapy described herein takes advantage of the procaspase-1 activation by PAC-1, which can synergize with the chemotherapeutic properties of a second active agent, to provide efficacy under conditions where one of the actives alone might be less effective or completely ineffective. These compounds can also be successful in targeted cancer therapy, where there can be advantages of selectivity in the killing of cancer cells with comparably reduced adverse reactions to non-cancerous cells having lower levels of procaspase-3. These adverse reactions can include toxicity, particularly neurotoxicity.

The combination of compounds, compositions and methods described herein can act via modulation of apoptosis or programmed cell death and other chemotherapeutic mechanisms to be effective in the treatment of cancer cells. In one embodiment, the modulation of apoptosis is by induction or activation of apoptosis. In various embodiments, the administration of compounds can be concurrent, or alternatively, sequential.

The invention thus provides methods for potentiation of an active agent by PAC-1, for example, for the treatment of lymphoma, osteosarcoma, or breast cancer. During apoptosis, the zymogen procaspase-3 is activated via proteolysis to caspase-3, and this active caspase-3 then cleaves scores of cellular substrates, executing the apoptotic program. Because procaspase-3 protein levels are elevated in various tumor histologies, drug-mediated direct activation of procaspase-3 can be highly effective as a selective anticancer strategy.

Certain compounds can enhance the activity and automaturation of procaspase-3 and induce apoptosis in cancer cells. Procaspase-activating compound-1 (PAC-1, FIG. 1) enhances the activity of procaspase-3 via the chelation of inhibitory zinc ions, induces apoptosis in cancer cells in culture, and has efficacy in multiple murine tumor models. Novel combinations of PAC-1 and several therapeutic agents have been found to be synergistically effective in treating cancer cells, particularly lymphoma, osteosarcoma, and breast cancer cells, as described herein. Because PAC-1 acts late in the apoptotic cascade, it is uniquely capable of synergizing with a wide range of chemotherapeutic active agents, as described below.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

"Concurrently" means (1) simultaneously in time, or (2) at different times during the course of a common treatment schedule.

"Sequentially" refers to the administration of one active agent used in the method followed by administration of another active agent. After administration of one active agent, the next active agent can be administered substantially immediately after the first, or the next active agent can be administered after an effective time period after the first active agent; the effective time period is the amount of time given for realization of maximum benefit from the administration of the first active agent.

An "effective amount" refers to an amount effective to treat a disease, disorder, and/or condition, or to bring about a recited effect, such as activation or inhibition. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. In one embodiment, an effective amount refers to an amount of the active agent described herein that are effective, either alone or in combination with a pharmaceutical carrier, upon single- or multiple-dose administration to a cell or a subject, e.g., a patient, at inhibiting the growth or proliferation, inducing the killing, or preventing the growth of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate. In some embodiments, the terms "treatment", "treat" or "treated" can refer to (i) prevention of tumor growth or regrowth of the tumor (prophylaxis), (ii) a reduction or elimination of symptoms or the disease of interest (therapy) or (iii) the elimination or destruction of the tumor (cure).

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting. Additionally, the terms "induce," "inhibit," "potentiate," "elevate," "increase," "decrease," or the like denote quantitative differences between two states, and can refer to at least statistically significant differences between the two states. For example, "an amount effective to inhibit the growth of hyperproliferative cells" means that the rate of growth of the cells can be, in some embodiments, at least statistically significantly different from the untreated cells. Such terms can be applied herein to, for example, rates of proliferation.

The phrase "inhibiting the growth or proliferation" of the hyperproliferative cell, e.g. neoplastic cell, refers to the slowing, interrupting, arresting, or stopping its growth and metastasis, and does not necessarily indicate a total elimination of the neoplastic growth.

The term "cancer" generally refers to any of a group of more than 100 diseases caused by the uncontrolled growth of abnormal cells. Cancer can take the form of solid tumors and lymphomas, and non-solid cancers such as leukemia. Unlike normal cells, which reproduce until maturation and then only as necessary to replace wounded cells, cancer cells can grow and divide endlessly, crowding out nearby cells and eventually spreading to other parts of the body.

The invention provides methods for treating cancer and cancerous conditions. The term "cancerous condition" relates to any condition where cells are in an abnormal state or condition that is characterized by rapid proliferation or neoplasia. A cancerous condition may be malignant or non-malignant (e.g. precancerous condition) in nature. To farther describe a "cancerous condition", the terms "hyperproliferative", "hyperplastic", "hyperplasia", "malignant", "neoplastic" and "neoplasia" can be used. These terms can be used interchangeably and are meant to include all types of hyperproliferative growth, hyperplastic growth, cancerous growths or oncogenic processes, metastatic tissues or malignantly transformed cells, tissues or organs, irrespective of histopathologic type, stage of invasiveness, or cancerous determination (e.g. malignant and nonmalignant).

The term "neoplasia" refers to new cell growth that results in a loss of responsiveness to normal growth controls, e.g., neoplastic cell growth. A "hyperplasia" refers to cells undergoing an abnormally high rate of growth. However, these terms can be used interchangeably, as their context will reveal, referring generally to cells experiencing abnormal cell growth rates. "Neoplasias" and "hyperplasias" include tumors, which may be either benign, premalignant, carcinoma in-situ, malignant, solid or non-solid. Examples of some cancerous conditions that are within the scope of the invention include, but are not limited to, anal cancer, transitional cell bladder cancer, bone cancer, breast cancer, cervical cancer, colorectal cancer, gastric cancer, head and neck cancer, Kaposi's sarcoma, leukemia, lung cancer such as bronchogenic lung cancer, small cell lung cancer, and non-small cell lung cancer, Hodgkin's lymphoma, Non-Hodgkin's lymphoma, malignant lymphoma, neuroblastomas, osteogenic carcinomas (e.g. cancer of the bone), ophthalmic cancers (e.g. retinoblastomas and other cancers of the eye), ovarian cancer, prostate cancer, renal cancer, skin cancers such as melanoma, soft tissue sarcomas, thyroid cancer, and Wilms' tumor. Other examples of non-malignant hyperproliferative conditions (e.g. precancerous conditions) that are within the scope of the invention include, but are not limited to, adenomas, chondromas, enchondromas, fibromas, myomas, myxomas, neurinomas, osteoblastomas, osteochondromas, osteomas, papillary tumors, and the like.

The terms "leukemia" or "leukemic cancer" refer to all cancers or neoplasias of the hematopoetic and immune systems (blood and lymphatic system). These terms refer to a progressive, malignant disease of the blood-forming organs, marked by distorted proliferation and development of leukocytes and their precursors in the blood and bone marrow. Myelomas refer to other types of tumors of the blood and bone marrow cells. Lymphomas refer to tumors of the lymph tissue. Examples of leukemia include acute myelogenous leukemia (AML), acute lymphoblastic leukemia (ALL), and chronic myelogenous leukemia (CML).

As described herein, the compositions and methods of the invention can be used for the treatment or prevention of various neoplasia disorders including such conditions as acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, sub-mesothelial, superficial spreading melanoma, undifferentiated carcinoma, uveal melanoma, verrucous carcinoma, vipoma, well differentiated carcinoma, and Wilm's tumor. Accordingly, the compositions and methods described herein can be used to treat bladder cancer, brain cancer (including intracranial neoplasms such as glioma, meninigioma, neurinoma, and adenoma), breast cancer, colon cancer, lung cancer (SCLC or NSCLC) ovarian cancer, pancreatic cancer, and prostate cancer.

In some embodiments, the combination of PAC-1 and a second active agent (e.g., a chemotherapeutic agent recited herein) can be particularly effective for treating cancers of the brain. Cancers of the brain include, but are not limited to, oligodendrogliomas and glioblastomas including glioblastoma multiforme (GBM). Tissues affected by the cancerous cells can be in the brain itself (e.g., the cranium or the central spinal canal) or in lymphatic tissue, in blood vessels, in the cranial nerves, in the brain envelopes (meninges), skull, pituitary gland, or pineal gland. Specific forms of brain cancer that can be treated include astrocytomas, chondromas, chondrosarcomas, chordomas, CNS (central nervous system) lymphomas, craniopharyngiomas, ependymomas, ganglioglio-mas, ganglioneuromas (also called gangliocytomas), gliomas, including astrocytomas, oligodendrogliomas, and ependymomas, hemangioblastomas (also called vascular tumors), primitive neuroectodermal tumors (PNET) such as medulloblastomas, meningiomas, and vestibular schwannomas (formerly known as acoustic neuroma/schwannoma).

The combination can also be used to treat metastatic tumors that invade the intracranial sphere from cancers originating in other organs of the body. These conditions are typically referred to as secondary brain tumors. Secondary brain tumors that can be treated with the combination of PAC-1 and a second active agent include metastatic tumors of the brain that originate from lung cancer, breast cancer, malignant melanoma, kidney cancer, colon cancer, and other carcinomas.

Other examples of cancerous conditions that are within the scope of the invention include, but are not limited to, neuroblastomas and osteogenic carcinomas (e.g. cancer of the bone or neoplastic growth of tissue in bone). Examples of malignant primary bone tumors that can be treated with the combination of PAC-1 and a second active agent include osteosarcomas, chondrosarcomas, Ewing's sarcoma, fibrosarcomas, and the like, and secondary bone tumors such as metastatic lesions that have spread from other organs, including carcinomas of the breast, lung, and prostate.

Therapeutic Agents and Activity

Procaspase-activating compound-1 (PAC-1; (2-(4-benzylpiperazin-1-yl)-N-[(2-hydroxy-3-prop-2-enyl-phenyl)methylideneamino]acetamide) selectively induces apoptosis in cancerous cells. The structure of PAC-1 is shown in FIG. 1 and methods of preparing PAC-1 are described in U.S. Patent Publication No. 2012/0040995 (Hergenrother et al.).

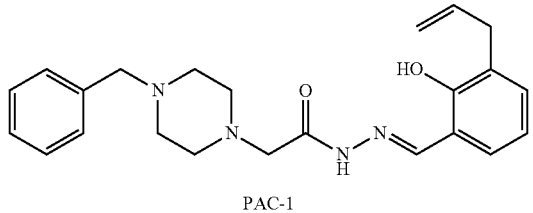 [SMILES: C=CCc1cccc(/C=N/NC(=O)CN2CCN(Cc3ccccc3)CC2)c1O]

PAC-1

PAC-1 enhances the activity of procaspase-3 via the chelation of inhibitory zinc ions, induces apoptosis in cancer cells. PAC-1 can enhance the activity and automaturation of procaspase-3 and induce apoptosis in cancer cells. PAC-1 also enhanced that chemotherapeutic activity of several other drugs, often where either PAC-1 or the second active is less effective or completely inactive alone. Accordingly, it was surprisingly discovered that PAC-1 synergizes the activity of numerous classes of chemotherapeutic agents. Examples of classes of compounds that can synergize with PAC-1 include:

(a) bcl-2 family inhibitors/modulators (including bax and bcl-xl inhibitors);

(b) modulators of BIR motif containing proteins (e.g., survivin, SMAC mimetics, and the like);

(c) modulators/stabilizers or inhibitors of microtubules or cytoskeletal elements (e.g., taxanes such as paclitaxel and docetaxel);

(d) alkylating agents such as cyclophosphamide, DTIC or cytotoxic antibiotics such as doxorubicin;

(e) DNA intercalating agents (e.g. platins such as cisplatin, carboplatin or oxaliplatin);

(f) autophagy modulating agents such as temozolomide;

(g) tumor cell signal transduction inhibitors (e g inhibitors or wild type or mutant EGFRs, braf, Ras, AKT, cMET, mTOR, PI3K, BTK, JAK/STAT family members, MEK);

(h) inhibitors/modulators of signaling receptors (e.g. tamoxifen, antibodies to EGFRs, CD20, CD19, and others over expressed or routinely expressed on tumor cells);

(i) inhibitors/modulators of angiogenesis (e.g., VEGFs, VEGFRs, angiogenins, angiostatins, TIE proteins, endostatins, and the like);

(j) modulators of immune mediated mechanism (e.g., vaccines, cell therapies, checkpoint inhibitors, pro-inflammatory cytokines/antibodies, adjuvants, and the like); and (k) proteasome inhibitors such as bortezomib.

Examples of specific chemotherapeutic agents (active agents, or 'second active agents') and can advantageously combined with PAC-1 include active agents such as, cisplatin, etoposide, irinotecan, camptostar, topotecan, paclitaxel, docetaxel, epothilones, taxotere, tamoxifen, 5-fluorouracil, methoxtrexate, temozolomide, cyclophosphamide, SCH 66336, R115777, L778,123, BMS 214662, gefitinib, erlotinib hydrochloride, antibodies to EGFR, imatinib, intron, ara-C, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, L-asparaginase, teniposide, ethinyl estradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, hydroxyurea, amsacrine, procarbazine, mitotane, mitoxantrone, levamisole, navelbene, anastrazole, letrazole, capecitabine, reloxafine, droloxafine, hexamethylmelamine, bevacizumab, herceptin, Bexxar, Zevalin, Trisenox, Xeloda, Vinorelbine, Porfimer, cetuximab, Thiotepa, Altretamine, Melphalan, Trastuzumab, Lerozole, Fulvestrant, Exemestane, Fulvestrant, Ifosfomide, Rituximab, C225, Campath, carboplatin, procarbazine, mechlorethamine, cyclophosphamide, camptothecin, busulfan, nitrosurea, plicomycin, mitomycin, raloxifene, estrogen receptor binding agents, navelbine, farnesyl-protein transferase inhibitors, transplatinum and methotrexate, or any analog or derivative variant of the foregoing.

Examples of chemotherapeutic active agent that show significant activity when combined with PAC-1 or a PAC-1 derivative include etoposide, bortezomib, staurosporine, doxorubicin, tamoxifen, cisplatin, carboplatin, paclitaxel, and SMAC mimetic.

Combination with Etoposide

Figure 2:
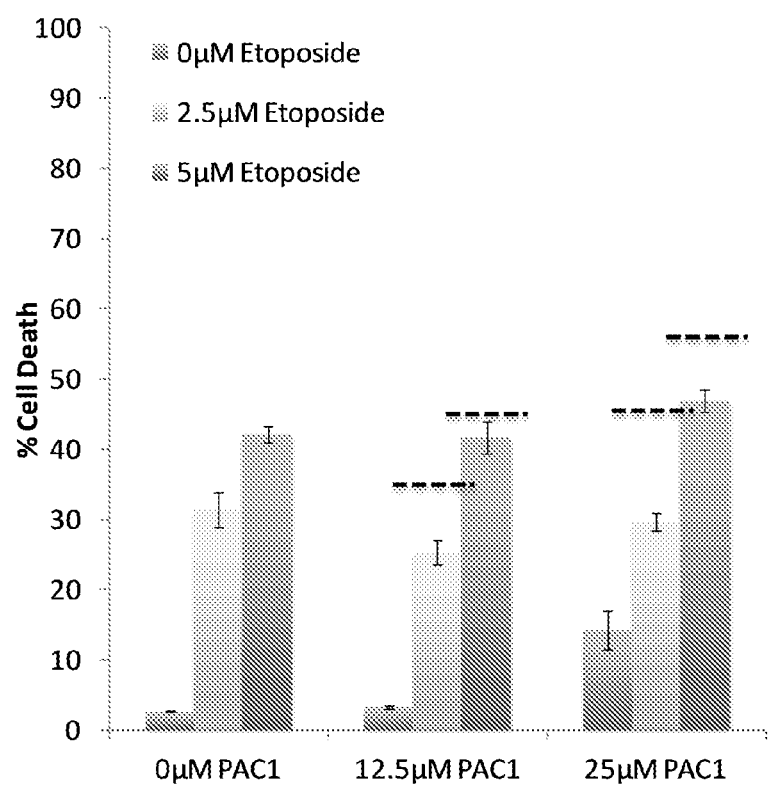
FIG. 2. Effects of PAC-1 with Etoposide on U-937 (lymphoma) cell death. Dashed lines represent the level of purely additive effects. The legend corresponds to the bars of the bar graph as follows: left bar=0 µM etoposide; middle bar=2.5 µM etoposide; right bar=5 µM etoposide.

Etoposide is a topoisomerase II inhibitor. Etoposide forms a ternary complex with DNA and the topoisomerase II enzyme, preventing re-ligation of the DNA strands, which causes errors in DNA synthesis and promotes apoptosis of the cancer cell. Combined treatment of U-937 cells with PAC-1 and etoposide showed significant in vitro activity even at low micromolar concentrations (FIG. 2).

Combination with Bortezomib

Figure 3:
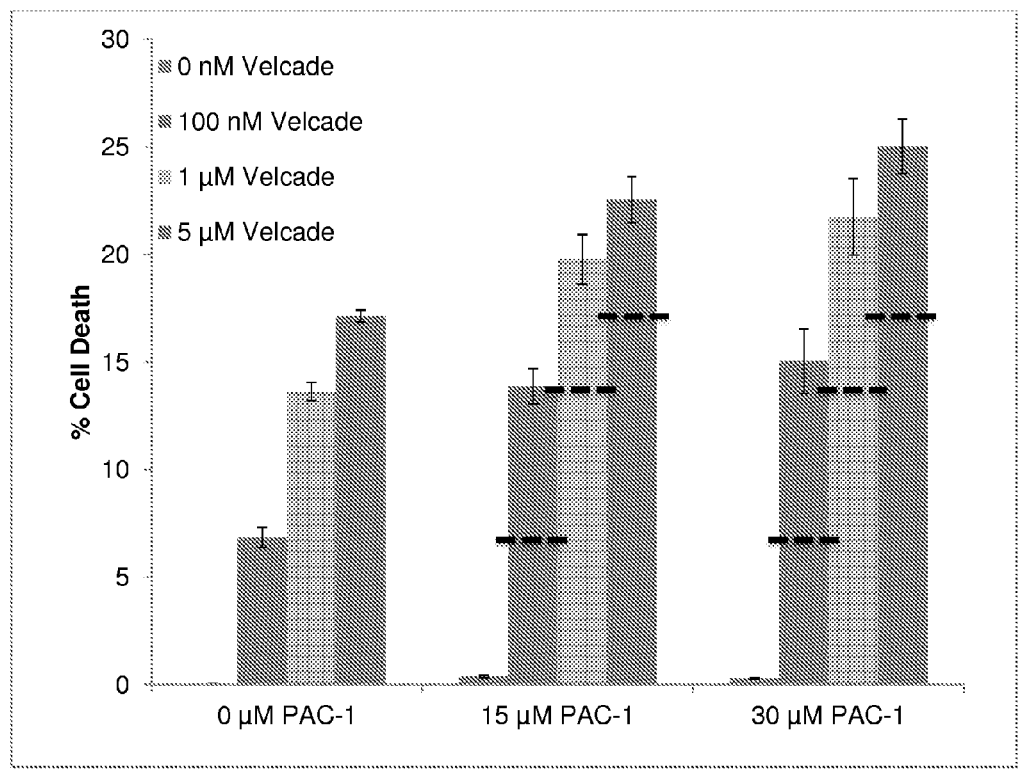
FIG. 3. Effects of PAC-1 with Velcade® (bortezomib) on U-937 (lymphoma) cell death. No cell death was observed for 0 nM bortezomib at 0 µM PAC-1. Cell death was measured after 6 hours in bortezomib. Dashed lines represent the expected level of purely additive effects; the combination therefore shows synergy at therapeutically relevant concentrations.

Velcade® (bortezomib) binds the catalytic site of the 26S proteasome with high affinity and specificity. In normal cells, the proteasome regulates protein expression and function by degradation of ubiquitinylated proteins, and also cleanses the cell of abnormal or misfolded proteins. While multiple mechanisms are likely to be involved, proteasome inhibition may prevent degradation of pro-apoptotic factors, permitting activation of programmed cell death in neoplastic cells dependent upon suppression of pro-apoptotic pathways. Synergistic activity was observed for the combination treatment of U-937 lymphoma cells with PAC-1 and bortezomib (FIG. 3).

Combination with Staurosporine

Figure 4:
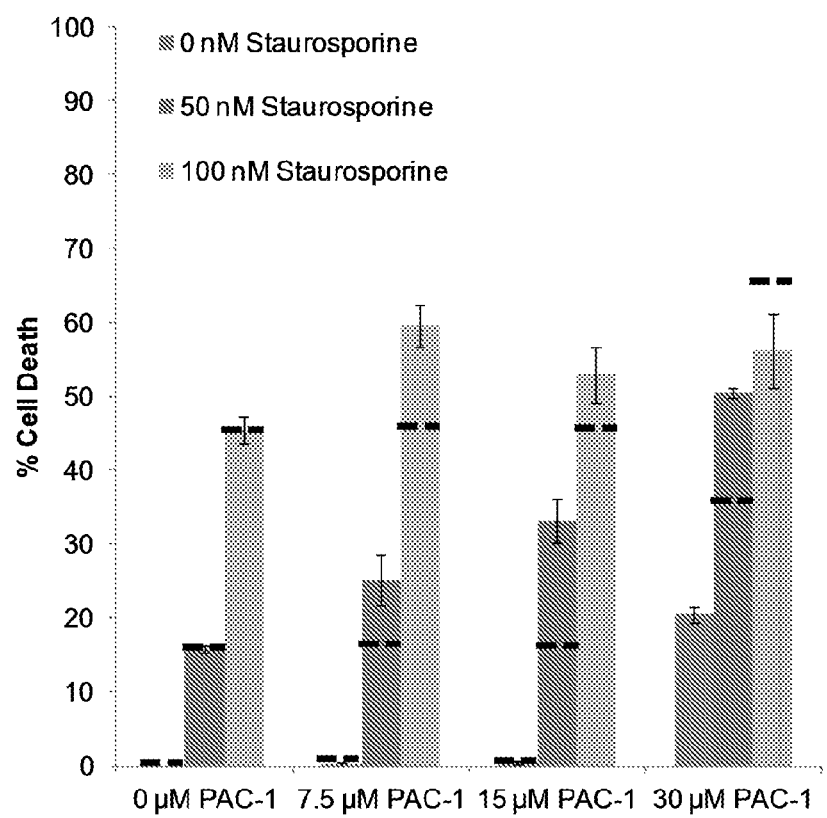
FIG. 4. Effects of PAC-1 with staurosporine on U-937 (lymphoma) cell death. Little or no cell death was observed for 0 nM bortezomib at 0-15 µM PAC-1. Cell death was measured after 8 hours in staurosporine. Dashed lines represent the expected level of purely additive effects; the combination therefore shows synergy at therapeutically relevant concentrations.

The main biological activity of staurosporine is the inhibition of protein kinases through the prevention of ATP binding to the kinase, which is achieved through the stronger affinity of staurosporine to the ATP-binding site on the kinase. Staurosporine is a prototypical ATP-competitive kinase inhibitor in that it binds to many kinases with high affinity, though with low selectivity. The lack of specificity has precluded its clinical use but has made it a valuable research tool where staurosporine is used to induce apoptosis. One way that staurosporine induces apoptosis is by activating caspase-3. Combined treatment of U-937 lymphoma cells with PAC-1 and staurosporine showed synergistic effects at low PAC-1 concentrations, such as at 7.5 µM and 15 µM PAC-1 (FIG. 4).

Combination with Doxorubicin

Figure 5:
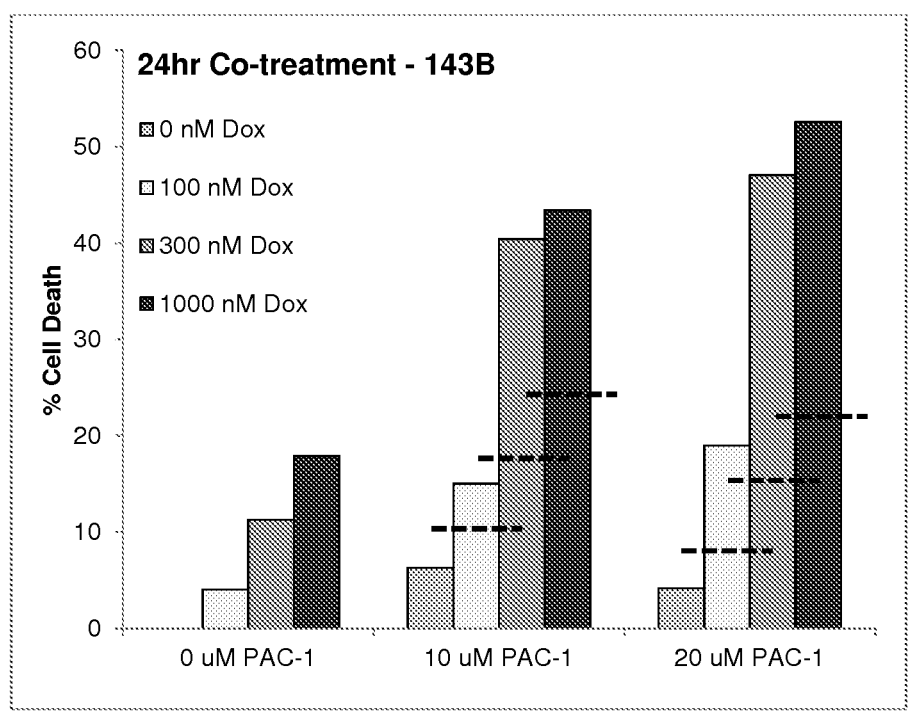
FIG. 5. PAC-1 synergizes with doxorubicin to kill osteosarcoma 143B (human OS) cells. The legend corresponds to the bars of the bar graph where the top legend entry corresponds to the left-most bar, and the remaining legend entries correspond to the remaining bars, top to bottom corresponding to left to right, respectively. No cell death was observed at 0 nM Dox with 0 µM PAC-1. Dashed lines represent the level of purely additive effects; the combination therefore shows synergy at therapeutically relevant concentrations.

Doxorubicin is an anthracycline antibiotic that exerts its cytotoxic activity by DNA intercalation. Doxorubicin is used to treat a wide range of cancers, including hematological malignancies, many types of carcinoma, and soft tissue sarcomas and osteosarcomas. Synergistic activity was observed for the combination treatment of 143B (human OS) osteosarcomas cells with PAC-1 and doxorubicin (FIG. 5).

Combination with Tamoxifen

Figure 6:
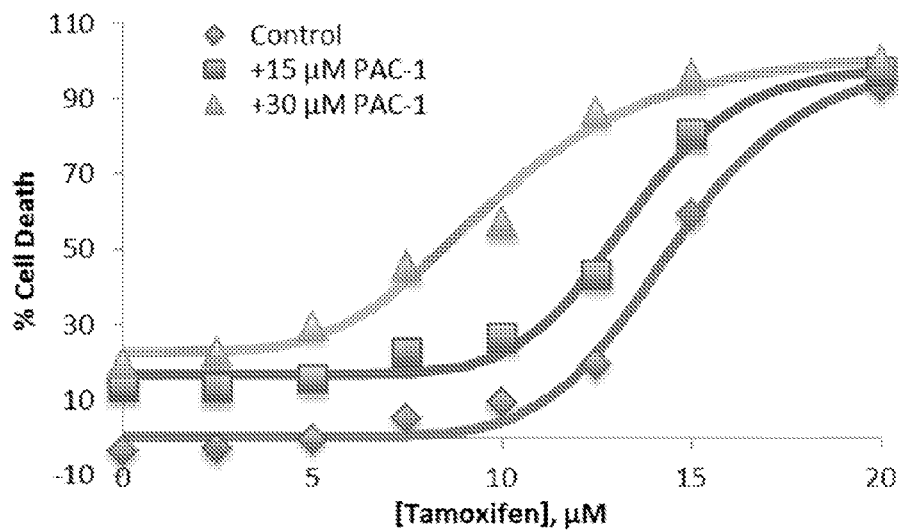
FIG. 6. PAC-1 potentiates tamoxifen in BT20 (triple negative breast cancer) cells, assessed at 36 hours at various PAC-1 and tamoxifen concentrations.
Figure 7:
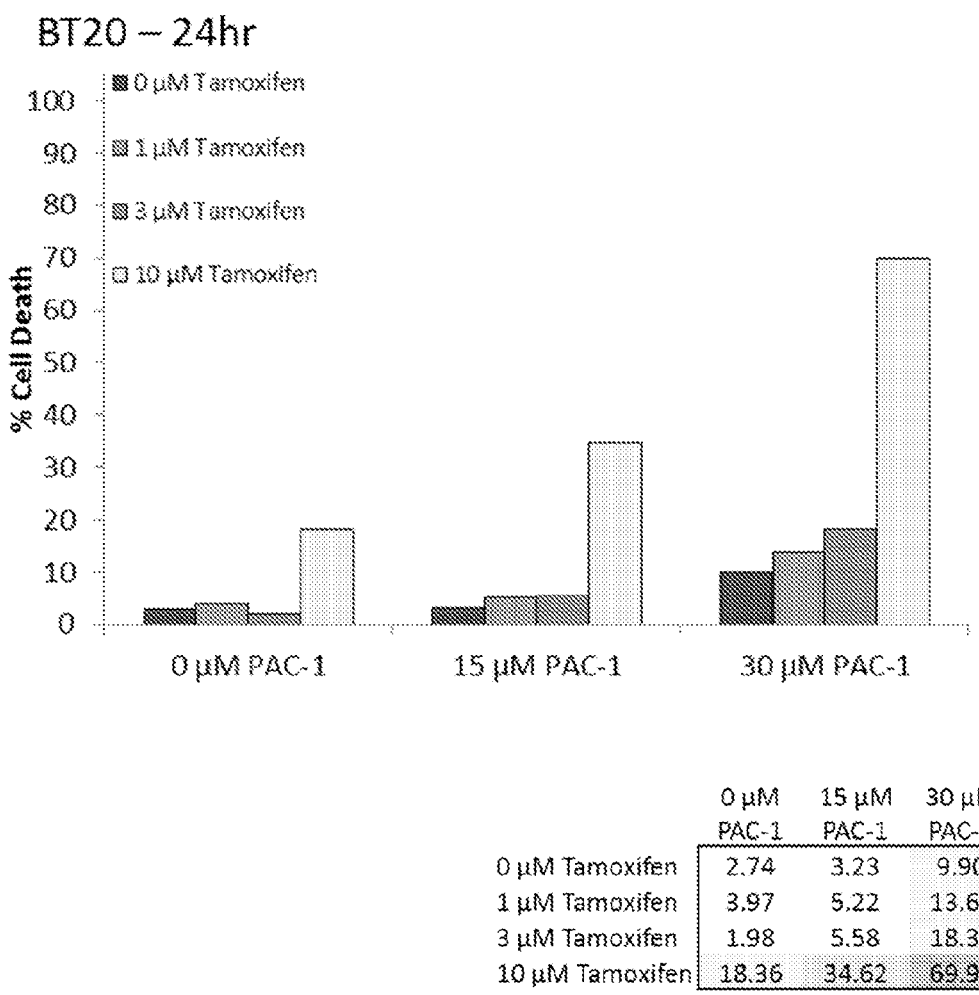
FIG. 7. The combination of PAC-1 and tamoxifen is synergistic for killing BT20 (triple negative breast cancer) cells, assessed at 24 hours at various PAC-1 and tamoxifen concentrations. The legends correspond to the bars of the bar graph where the top legend entry corresponds to the left-most bar, and the remaining legend entries correspond to the remaining bars, top to bottom corresponding to left to right, respectively.
Figure 8:
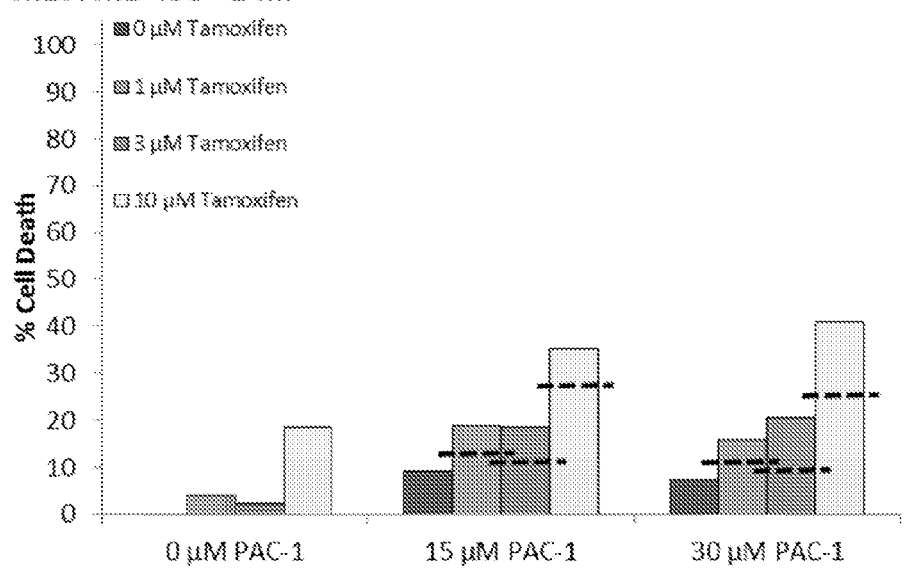
FIG. 8. The combination of PAC-1 and tamoxifen is synergistic for killing MDA MB 436 (triple negative breast cancer) cells, assessed at 24 hours at various PAC-1 and tamoxifen concentrations. The legends correspond to the bars of the bar graph where the top legend entry corresponds to the left-most bar, and the remaining legend entries correspond to the remaining bars, top to bottom corresponding to left to right, respectively.

Tamoxifen, a competitive agonist of estrogen receptor is the most common treatment for male breast cancer and is used for both early and advanced ER+ breast cancers. Tamoxifen is approved for the prevention of breast cancer in those at high risk. The combination of tamoxifen and PAC-1 is synergistic and provides enhanced cell killing efficiencies in breast cancer, including tamoxifen negative or tamoxifen resistant breast cancer, and triple negative breast cancer (FIGS. 6-8).

Combination with Cisplatin

Figure 9:
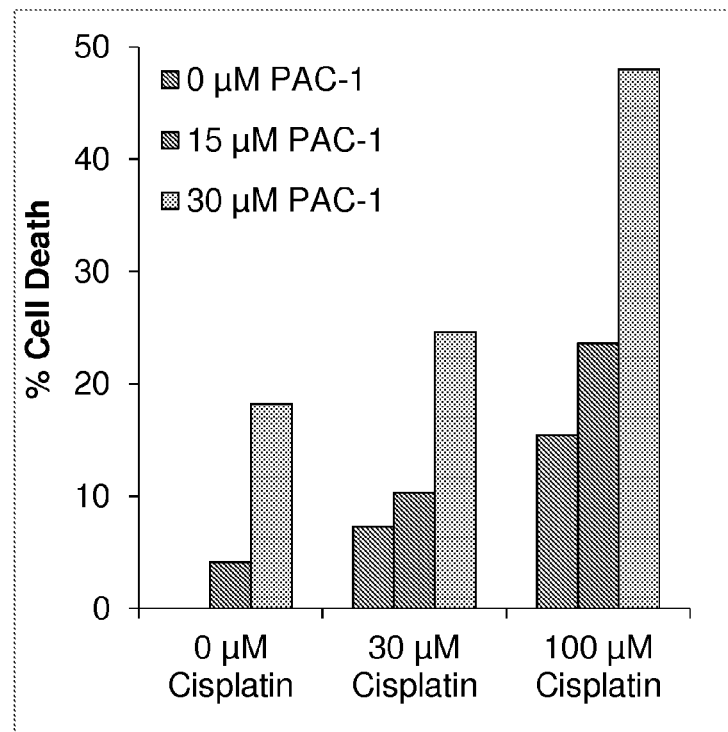
FIG. 9. The combination of PAC-1 and cisplatin is synergistic for killing IGROV-1 (ovarian carcinoma) cells, assessed at 40 hours (Annexin V/PI staining) at various PAC-1 and cisplatin concentrations. The legends correspond to the bars of the bar graph where the top legend entry corresponds to the left-most bar (absent at 0 µM cisplatin), and the remaining legend entries correspond to the remaining bars, top to bottom corresponding to left to right, respectively.

Cisplatin is one of several platinum coordination complexes that are used in cancer chemotherapy. The cytotoxicity of platinum compounds can result from inhibition of DNA synthesis in cancer cells. Cisplatin is used for the treatment of various types of cancers, including sarcomas, carcinomas (including small cell lung cancer and ovarian cancer), lymphomas, germ cell tumors, and testicular cancer. The combination of cisplatin and PAC-1 can be synergistic and can provide enhanced cell killing efficiencies in these treatments as well as ovarian carcinoma (FIG. 9).

Combination with Paclitaxel

Figure 10:
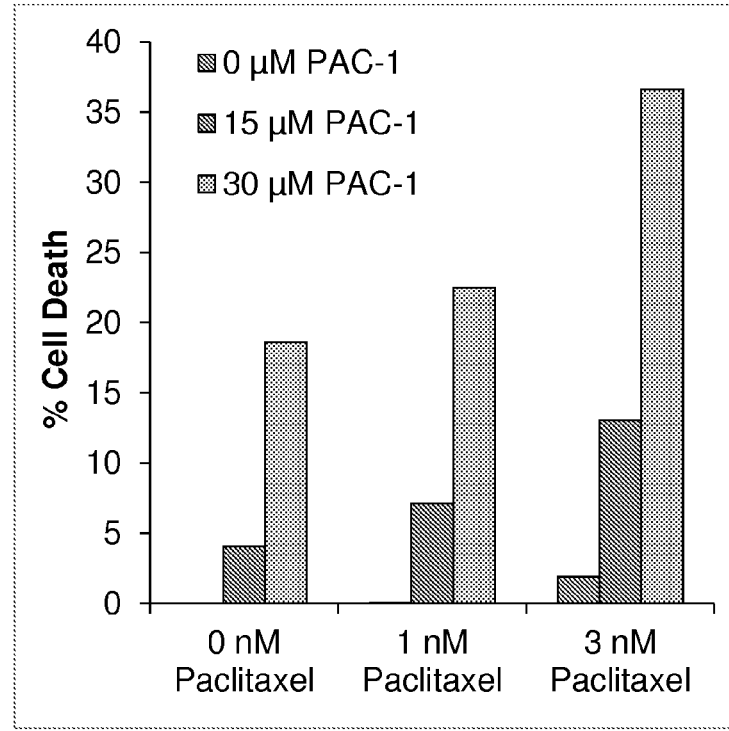
FIG. 10. The combination of PAC-1 and paclitaxel is synergistic for killing IGROV-1 (ovarian carcinoma) cells, assessed at 40 hours (Annexin V/PI staining) at various PAC-1 and paclitaxel concentrations. The legends correspond to the bars of the bar graph where the top legend entry corresponds to the left-most bar (absent at 0 µM paclitaxel), and the remaining legend entries correspond to the remaining bars, top to bottom corresponding to left to right, respectively.

Paclitaxel, a mitotic inhibitor (microtubule stabilizer), is used in the treatment of lung, ovarian, breast, and head and neck cancer. Paclitaxel is recommended for the treatment of advanced breast cancer after failure of anthrocyclines and is recommended against use in early node-positive breast cancer. The combination of paclitaxel and PAC-1 provides synergistic activity and enhanced cell killing efficiencies in these treatments as well as ovarian carcinoma (FIG. 10).

Combination with Carboplatin

Figure 11:
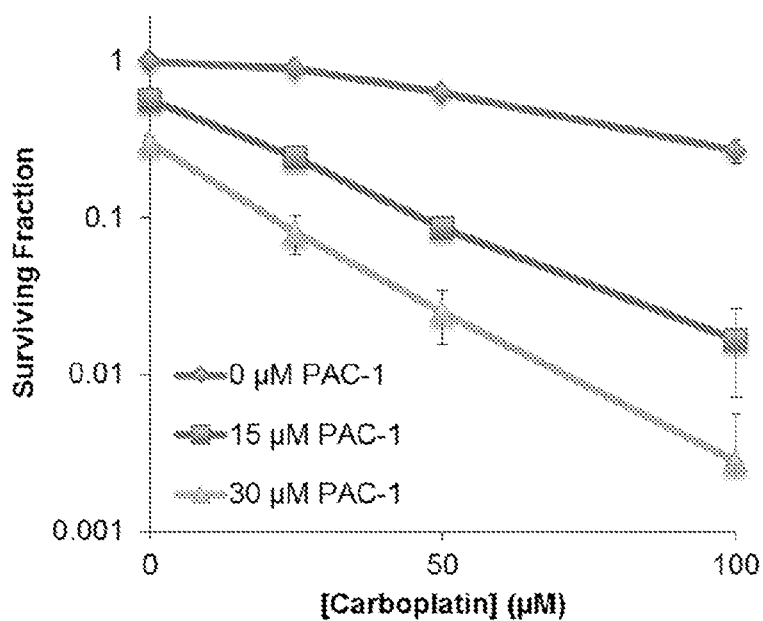
FIG. 11. PAC-1 synergizes with carboplatin to induce death of HOS (human osteosarcoma) cells in culture. Cells were co-treated for 8 hours, media was replaced and colonies were allowed 7 days to grow.
Figure 12:
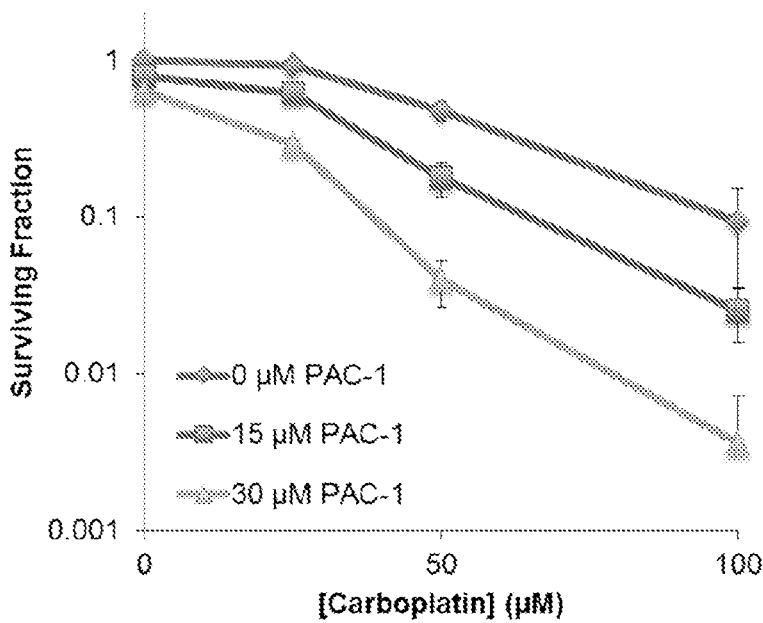
FIG. 12. PAC-1 synergizes with carboplatin to induce death of 143B (human osteosarcoma) cells in culture. Cells were co-treated for 8 hours, media was replaced and colonies were allowed 7 days to grow.

Carboplatin is another one of the several platinum coordination complexes that are used in cancer chemotherapy. Carboplatin is used for the treatment of various types of cancers, mainly ovarian carcinoma, lung, head and neck cancers. The combination of carboplatin and PAC-1 is synergistic and can provide enhanced cell killing efficiencies in these treatments as well as osteosarcoma (FIGS. 11 and 12).

Further Combination Studies

Utilizing cell lines that represent of 12 of the 17 recently defined breast cancer subtypes (Table 1), examination of non-lethal doses of PAC-1 sensitization/synergy with standard of care drugs is underway.

TABLE 1

Breast cancer cell lines under investigation.

| Subgroup | Cell Line |
|---|---|
| 5 | BT20 |
| 5 | BT549 |
| 5 | Hs578T |
| 2 | HCC1569 |
| 4 | MCF7 |
| 4 | T47D |
| 6 | MDAMB361 |
| 7 | AU565 |

TABLE 1-continued

Breast cancer cell lines under investigation.

| Subgroup | Cell Line |
|---|---|
| 8 | HCC1954 |
| 9 | MDAMB231 |
| 10 | HCC202 |
| 14 | MDAMB436 |
| 16 | BT483 |

PAC-1 combined with a variety of different standard of care agents can also provide additive or synergistic activity that may not be otherwise obtainable. Examples of such standard of care agents being investigated for combination effects include:

Lapatinib, a dual tyrosine kinase inhibitor (EGFR and HER2) is used in therapy for HER2 positive cancers and front line therapy for triple positive breast cancers. The combination of lapatinib and PAC-1 can provide enhanced cell killing efficiencies in these treatments.

Fluorouracil (5-FU) is a pyrimidine analog drug that is used in the treatment of a variety of cancers. It is a suicide inhibitor and works through irreversible inhibition of thymidylate synthase. The combination of 5-FU and PAC-1 can provide enhanced cell killing efficiencies in cancers treatable by 5-FU.

In various embodiments, PAC-1 can be exchanged with its analog SPAC-1 for similar enhanced, additive, or synergistic activity. The combination effects of SPAC-1 with common oncological therapies against colon, lung and liver cancer cell lines are being investigated. Examples of the combination agents, cell lines and data output that can be obtained are summarized in Table 2 and Table 3, where, for example, PAC-1 or SPAC-1 can be combined with any of Standard Agents 1-4.

Active agents that can be combined with PAC-1 or a derivative thereof to provide enhanced or synergistic activity for inhibiting cancer cell growth or for treating a particular type of cancer further include:

SN-38 is the active metabolite of irinotecan (an analog of camptothecin, a topoisomerase I inhibitor). SN-38 is 200 times more active than irinotecan itself. Irinotecan's main use is in colon cancer, in particular, in combination with other chemotherapy agents. The combination of SN-38 and PAC-1 can provide enhanced cell killing efficiencies in these treatments.

Oxaliplatin is one of several platinum coordination complexes that are used in cancer chemotherapy. The cytotoxicity of platinum compounds is thought to result from inhibition of DNA synthesis in cancer cells. In vivo studies showed that oxaliplatin has anti-tumor activity against colon carcinoma through its (non-targeted) cytotoxic effects. The combination of oxaliplatin and PAC-1 can provide enhanced cell killing efficiencies in these treatments.

Sorafenib is a small molecular inhibitor of several Tyrosine protein kinases (VEGFR and PDGFR) and Raf. Sorafenib targets the MAP kinase pathway (Raf/Mek/Erk pathway) (MAP Kinase pathway) and is approved for the treatment of primary kidney cancer (advanced renal cell carcinoma) and advanced primary liver cancer (hepatocellular carcinoma). The combination of sorafenib and PAC-1 can provide enhanced cell killing efficiencies in these treatments.

Sunitinib is an oral, small-molecule, multi-targeted receptor tyrosine kinase (RTK) inhibitor that was approved by the FDA for the treatment of renal cell carcinoma (RCC) and imatinib-resistant gastrointestinal stromal tumor (GIST). The combination of sunitinib and PAC-1 can provide enhanced cell killing efficiencies in these treatments.

Gemcitabine is a nucleoside analog used for chemotherapy. As with fluorouracil and other analogues of pyrimidines, the triphosphate analogue of gemcitabine replaces one

TABLE 2

Cell lines and agents for Combination effects.

| Cell Line | Tissue | Std. Agent 1 | Std.Agent 2 | Std. Agent 3 | Std Agent 4 |
|---|---|---|---|---|---|
| DLD-1 (BIRC5↑) | Colon | SN-38 | Oxaliplatin | | |
| HCT-116 | Colon | SN-38 | Oxaliplatin | | |
| Hep3B | Liver | Sorafenib | Sunitinib | | |
| HepG2 | Liver | Sorafenib | Sunitinib | | |
| A549 (NSCL-AC) | Lung | Oxaliplatin | Gemcitabine | Erlotinib | Pemetrexed |
| H292 (NSCL-C) | Lung | Oxaliplatin | Gemcitabine | Erlotinib | Pemetrexed |
| SK-MES-1 (SCC) | Lung | Oxaliplatin | Etoposide | Gemcitabine | |

TABLE 3

Data under investigation for combination effect experiments, where Drug 1 is PAC-1 or a derivative thereof and Drug 2 is an active agent recited or described herein.

| | | Drug 1 | | | | | |
|---|---|---|---|---|---|---|---|
| | | 0 | 0.25X ($IC_{50}$) | 0.5X ($IC_{50}$) | 1.0X ($IC_{50}$) | 2.0X ($IC_{50}$) | 4.0X ($IC_{50}$) |
| Drug 2 | 0 | Control | $(F_a)_1$ | $(F_a)_1$ | $(F_a)_1$ | $(F_a)_1$ | $(F_a)_1$ |
| | 0.25X ($IC_{50}$) | $(F_a)_2$ | $(F_a)_{1,2}$ | | | | |
| | 0.5X ($IC_{50}$) | $(F_a)_2$ | | $(F_a)_{1,2}$ | | | |
| | 1.0X ($IC_{50}$) | $(F_a)_2$ | | | $(F_a)_{1,2}$ | | |
| | 2.0X ($IC_{50}$) | $(F_a)_2$ | | | | $(F_a)_{1,2}$ | |
| | 4X ($IC_{50}$) | $(F_a)_2$ | | | | | $(F_a)_{1,2}$ |

$F_a$ = Fraction of cell affected by treatment of the building blocks of nucleic acids, in this case cytidine, during DNA replication. The process arrests tumor growth, as only one additional nucleoside can be attached to the "faulty" nucleoside, resulting in apoptosis. Another target of gemcitabine is the enzyme ribonucleotide reductase (RNR). The diphosphate analogue binds to the RNR active site and inactivates the enzyme irreversibly. Once RNR is inhibited, the cell cannot produce the deoxyribonucleotides required for DNA replication and repair, and cell apoptosis is induced. The combination of gemcitabine and PAC-1 can provide enhanced cell killing efficiencies in these treatments.

Erlotinib is a drug used to treat non-small cell lung cancer, pancreatic cancer and several other types of cancer. It is a tyrosine kinase inhibitor, which acts on the epidermal growth factor receptor (EGFR). The combination of erlotinib and PAC-1 can provide enhanced cell killing efficiencies in these treatments.

Pemetrexed is a chemotherapy drug used in the treatment of pleural mesothelioma as well as non-small cell lung cancer. Pemetrexed is in the class of chemotherapy drugs called folate antimetabolites. It works by inhibiting three enzymes used in purine and pyrimidine synthesis-thymidylate synthase (TS), dihydrofolate reductase (DHFR), and glycinamide ribonucleotide formyltransferase (GARFT). By inhibiting the formation of precursor purine and pyrimidine nucleotides, pemetrexed prevents the formation of DNA and RNA, which are required for the growth and survival of both normal cells and cancer cells. The combination of pemetrexed and PAC-1 can provide enhanced cell killing efficiencies in these treatments.

While there is clear benefit to anticancer strategies utilizing combinations of drugs that act on different targets, the work described herein demonstrates that dramatic synergy can be observed with compounds that act through disparate mechanisms. This multi-targeting approach can have particular advantages when activation of an enzyme is sought.

PAC-1 is safe in mammals, and a derivative of PAC-1 was efficacious in a phase I clinical trial of pet dogs with lymphoma (Peterson et al., Cancer Res 70, 7232-7241 (2010)), thus the observed synergy with active agents such as etoposide, bortezomib, staurosporine, doxorubicin, and tamoxifen will have significant clinical impact. Interest in activating enzymes with small molecules is increasing rapidly. The data described herein indicate that targeting strategies using PAC-1 and such complimentary active agents is a general approach for dramatic enhancement of the intended biologic effect and should have considerable clinical impact due to its efficacy.

Methods of the Invention

The invention provides methods of selectively inducing apoptosis in a cancer cell, comprising administering to a cancer cell a combination of compounds capable of modifying a procaspase-3 molecule of said cancer cell; wherein the combination of compounds is PAC-1 and a second active agent. Also provided is a method of selectively inducing apoptosis in a cancer cell, comprising administering to a cancer cell a combination of compounds capable of modifying a procaspase-3 molecule of the cancer cell; wherein the combination of compounds is PAC-1 and a second active agent, for example, wherein the cancer cell is in a patient in need of treatment.

The invention provides additional methods where the recited combination of compounds is PAC-1 and a second active agent, for example, as a method of treating a cancer cell, comprising (a) identifying a potential susceptibility to treatment of a cancer cell with a procaspase activator compound; and (b) exposing the cancer cell to an effective amount of a combination of a procaspase activator compound and a second active agent. Also provided is a method of treating a cancer cell, comprising (a) identifying a potential susceptibility to treatment of a cancer cell with a procaspase activator compound; and (b) exposing said cancer cell to an effective amount of PAC-1 and a second active agent; wherein the PAC-1 is capable of activating at least one of procaspase-3 and procaspase-7. Also provided is a method of inducing death in a cancer cell (e.g., killing a cancer cell), comprising administering to a cancer cell an active agent and a compound capable of activating a procaspase-3 molecule of the cancer cell, such as PAC-1.

The invention further provides a medicament comprising an effective amount of the combination of PAC-1 and a second active agent. The medicament can be used in a method of inducing apoptosis in a cell. In some embodiments, the combination of compounds does not cross the blood-brain barrier to as extent that causes appreciable neurotoxic effects in a patient. Methods of the invention include contacting one or more cells with an effective amount of a combination of compounds described herein, in vivo or in vitro. The invention thus also provides methods of treating a cell that include contacting a cell with an effective amount of a combination of compounds described herein.

As described herein, the invention provides methods of treating a patient that has tumor cells having elevated procaspase-3 levels. The methods can include administering to a patient having tumor cells with elevated procaspase-3 levels a therapeutically effective amount of a combination of PAC-1 and a second active agent described herein, or a composition thereof. The invention further provides methods of treating a tumor cell having an elevated procaspase-3 level comprising exposing the tumor cell to a therapeutically effective amount of a combination of PAC-1 and a second active agent described herein, wherein the tumor cell is treated, killed, or inhibited from growing. The tumor or tumor cells can be malignant tumor cells. In some embodiments, the tumor cells are lymphoma, osteosarcoma, or breast cancer cells.

PAC-1 can be combined with a second active agent in a unitary dosage form for the administration to a patient. The combination therapy may be administered as a simultaneous or sequential regimen. When administered sequentially, the combination may be administered in two or more administrations.

The combination therapy may provide "synergy", i.e. the effect achieved when the active ingredients used together is greater than the sum of the effects that results from using the compounds separately. A synergistic effect may be attained when PAC-1 and a second active agent are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient can be administered sequentially, i.e. serially, whereas in combination therapy, effective dosages of two or more active ingredients are administered together. A synergistic anti-cancer effect denotes an anti-cancer effect that is greater than the predicted purely additive effects of the individual compounds of the combination. Combination therapy is further described by U.S. Pat. No. 6,833,373 (McKearn et al.), which includes additional active agents that can be combined with PAC-1, and additional types of cancer and other conditions that can be treated with PAC-1.

Accordingly, PAC-1 can be used in combination with another active agent ("a second active agent") for cancer treatment. PAC-1 may precede or follow the second active agent administration by intervals ranging from minutes to weeks. In embodiments where the second active agent and PAC-1 are applied separately to the cell, one would generally ensure that a significant period of time did not elapse between the time of each delivery, such that the agent and PAC-1 would still be able to exert an advantageously combined effect on the cell. For example, in such instances, it is contemplated that one may contact the cell, tissue or organism with the two modalities substantially simultaneously (i.e., within less than about a few minutes). In other aspects, the second active agent of the combination may be administered within about 1 minute, about 5 minutes, about 10 minutes, about 20 minutes about 30 minutes, about 45 minutes, about 60 minutes, about 2 hours, about 3 hours, about 4 hours, about 6 hours, about 8 hours, about 9 hours, about 12 hours, about 15 hours, about 18 hours, about 21 hours, about 24 hours, about 28 hours, about 31 hours, about 35 hours, about 38 hours, about 42 hours, about 45 hours, or at about 48 hours or more, prior to and/or after administering PAC-1. In certain other embodiments, the second active agent may be administered within about 1 day, about 2 days, about 3 days, about 4 days, about 5 days, about 6 days, about 8 days, about 9 days, about 12 days, about 15 days, about 16 days, about 18 days, about 20 days, or about 21 days, prior to and/or after administering PAC-1. In some situations, it may be desirable to extend the time period for treatment significantly, however, where several weeks (e.g., about 1, about 2, about 3, about 4, about 6, or about 8 weeks or more) lapse between the respective administrations.

Administration of the chemotherapeutic compositions of the invention to a patient will typically follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described combinations. These therapies include but are not limited to chemotherapy, immunotherapy, gene therapy and surgery.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, a-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. The solubility of actives can be increase by the use of cyclodextrins, such as 2-hydroxypropyl-β-cyclodextrin. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 1% to about 60%, or about 2% to about 25%, of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The combination of compounds can be conveniently administered in a unit dosage form, for example, containing 100 to 5,000 mg/m$^2$, 300 to 4,000 mg/m$^2$, 370 to 3,700 mg/m$^2$, 50 to 750 mg/m$^2$, or 750 to 4,000 mg/m$^2$ of active ingredient per unit dosage form. Each compound, individually or in combination, can also be administered at about 1 mg/kg to about 250 mg/kg, about 10 mg/kg to about 100 mg/kg, about 10 mg/kg to about 50 mg/kg, about 50 mg/kg to about 100 mg/kg, about 10 mg/kg to about 50 mg/kg, or about 10 mg/kg, about 25 mg/kg, about 50 mg/kg, about 75 mg/kg, about 100 mg/kg, or about 150 mg/kg, or a range from any one of the aforementioned values to any other of the aforementioned values. The compounds can also be administered to a subject to provide a steady-state plasma concentration of the drugs, alone or in combination, of about 1 µmol/L to about 25 µmol/L, or about 10 µmol/L, or about 15 µmol/L.

In some embodiments, the invention provides the compounds in effective concentrations at about 10 nM to about 100 µM. In another embodiment, the effective concentrations are from about 200 nM to about 50 µM, about 500 nM to about 40 µM, about 750 nM to about 25 µM, about 1 µM to about 20 µM, or about 1 µM to about 10 µM. In another embodiment, the effective concentration is considered to be a value such as a 50% activity concentration in a direct procaspase activation assay, in a cell apoptosis induction assay, or in an animal clinical therapeutic assessment. In one embodiment, such value is less than about 200 µM. In another embodiment, the value is less than about 10 µM but greater than about 10 nM. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds described herein can be effective antitumor agents and have higher potency and/or reduced toxicity as compared to the administration of any single agent. The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, among others described herein, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using the assays described above and in the citations and patent documents cited herein.

The invention also provides prodrug forms of compounds. Any compound that will be converted in vivo to provide PAC-1 or another active agent recited herein is a prodrug. Numerous methods of forming prodrugs are well known in the art. Examples of prodrugs and methods of preparing them are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., *Journal of Pharmaceutical Sciences*, Vol. 77, p. 285 (1988); and Nogrady (1985) Medicinal Chemistry A Biochemical Approach, Oxford University Press, New York, pages 388-392).

Additionally, in some embodiments, PAC-1 can be exchanged for a PAC-1 derivative or other inhibitor, such as a compound described in U.S. Pat. No. 7,632,972 (Hergenrother et al.), U.S. Patent Publication Nos. 2012/0040995 (Hergenrother et al.) and 2007/0049602 (Hergenrother et al.), and U.S. application Ser. No. 12/597,287 (Hergenrother et al.). Useful compounds, methods, and techniques for cancer therapy that can be used in combination with the disclosure herein are described in the aforementioned documents, as well as in U.S. Pat. No. 6,303,329 (Heinrikson et al.), U.S. Pat. No. 6,403,765 (Alnemri), U.S. Pat. No. 6,878,743 (Choong et al.), and U.S. Pat. No. 7,041,784 (Wang et al.), and U.S. Patent Publication No. 2004/0180828 (Shi).

Methods for performing the tests and evaluating cancer cell lines can be carried out as described by Putt et al., *Nature Chemical Biology* 2006, 2(10), 543-550; Peterson et al., *J. Mol. Biol.* 2009, 388, 144-158; and Peterson et al., *Cancer Res.* 2010, 70(18), 7232-7241.

The following Example is intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Pharmaceutical Dosage Forms

The following formulations illustrate representative pharmaceutical dosage forms that may be used for the therapeutic or prophylactic administration of the combination compounds described herein (e.g., PAC-1 and the second active agent), or pharmaceutically acceptable salts or solvates thereof (hereinafter referred to as 'Compounds X'):

| (i) Tablet 1 | mg/tablet |
|---|---|
| 'Compounds X' | 200.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 400.0 |

| (ii) Tablet 2 | mg/tablet |
|---|---|
| 'Compounds X' | 120.0 |
| Microcrystalline cellulose | 410.0 |
| Starch | 50.0 |
| Sodium starch glycolate | 15.0 |
| Magnesium stearate | 5.0 |
| | 600.0 |

| (iii) Capsule | mg/capsule |
|---|---|
| 'Compounds X' | 110.0 |
| Colloidal silicon dioxide | 1.5 |
| Lactose | 465.5 |
| Pregelatinized starch | 120.0 |
| Magnesium stearate | 3.0 |
| | 700.0 |

| (iv) Injection 1 (1 mg/mL) | mg/mL |
|---|---|
| 'Compounds X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compounds X' | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compounds X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compounds X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition comprising:
   (a) about 15 µM to about 30 µM of PAC-1:

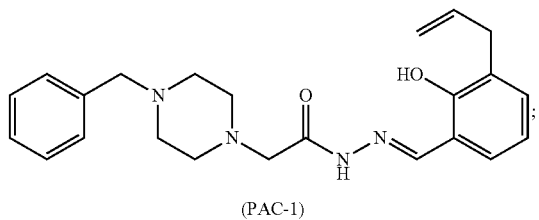 [SMILES: C=CCc1cccc(/C=N/NC(=O)CN2CCN(Cc3ccccc3)CC2)c1O]

(PAC-1)

(b) about 10 µM to about 15 µM of tamoxifen; and
   (c) a pharmaceutically acceptable diluent, excipient, or carrier.

2. The composition of claim 1 wherein the carrier comprises water and optionally a buffer, a cyclodextrin, or a combination thereof.

3. The composition of claim 2 wherein the cyclodextrin is 2-hydroxypropyl-β-cyclodextrin.

4. The composition of claim 1 wherein the concentration of PAC-1 is to about 30 µM.

5. The composition of claim 1, wherein the concentration of tamoxifen is about 10 µM.

* * * * *